United States Patent [19]

Nye

[11] Patent Number: 5,686,547

[45] Date of Patent: Nov. 11, 1997

[54] CARBONATE AND HYDROXY CARBAMATE FUNCTIONALIZED SILICONES

[75] Inventor: Susan A. Nye, Feura Bush, N.Y.

[73] Assignee: General Electric Company, Pittsfield, Mass.

[21] Appl. No.: 804,650

[22] Filed: Feb. 25, 1997

Related U.S. Application Data

[63] Continuation-in-part of Ser. No. 615,904, Mar. 14, 1996, abandoned.

[51] Int. Cl.$^6$ .................................................. C08G 77/08
[52] U.S. Cl. ................... 528/15; 528/26; 528/28; 525/474; 525/478; 525/479
[58] Field of Search .................... 528/15, 26, 28; 525/478, 479, 474

[56] References Cited

U.S. PATENT DOCUMENTS

| | | |
|---|---|---|
| 3,402,192 | 9/1968 | Haluska . |
| 3,494,951 | 2/1970 | Berger . |
| 3,517,001 | 6/1970 | Berger . |
| 3,642,855 | 2/1972 | Berger . |
| 3,821,218 | 6/1974 | Berger . |
| 4,090,987 | 5/1978 | Koerner . |
| 4,218,250 | 8/1980 | Kasprzak . |
| 4,265,878 | 5/1981 | Keil . |
| 4,266,046 | 5/1981 | Wu . |
| 4,268,499 | 5/1981 | Keil . |
| 4,311,695 | 1/1982 | Starch . |
| 4,421,656 | 12/1983 | Donatelli et al. . |
| 4,429,096 | 1/1984 | Schaefer . |
| 4,855,379 | 8/1989 | Budnik et al. . |
| 4,980,156 | 12/1990 | Raleigh et al. . |
| 4,988,504 | 1/1991 | Zotto et al. . |
| 5,008,103 | 4/1991 | Raleigh et al. . |
| 5,266,715 | 11/1993 | Harisiades et al. . |
| 5,312,943 | 5/1994 | Gaglani . |

FOREIGN PATENT DOCUMENTS

| | | |
|---|---|---|
| 0307605 | 3/1989 | European Pat. Off. . |
| 2173005 | 10/1973 | France . |
| 1237247 | 3/1967 | Germany . |
| 7304909 | 10/1973 | Netherlands . |
| 7601202 | 2/1976 | Netherlands . |
| 981812 | 1/1965 | United Kingdom . |
| 1034782 | 7/1966 | United Kingdom . |

OTHER PUBLICATIONS

Macromolecules 1994, 27, 4076–4079 – Synthesis of Polysiloxanes Bearing Cyclic Carbonate Side Chains.
Synthesis of Functional Polymers Bearing Cyclic Carbonate Groups from (2–Oxo–1,3–dioxolan–4–yl)methyl Vinyl Ether, Journal of Polymer Science, vol. 32 (1994), pp. 301–308.

*Primary Examiner*—Melvyn I. Marquis
*Attorney, Agent, or Firm*—Kenneth S. Wheelock

[57] ABSTRACT

Carbonate and hydroxy carbamate functionalized silicones and a process for their preparation are described. Hydroxy carbamate functionalized silicones are useful in personal care and cosmetic compositions.

21 Claims, No Drawings

CARBONATE AND HYDROXY CARBAMATE FUNCTIONALIZED SILICONES

CROSS-REFERENCE TO RELATED APPLICATIONS

This application is a Continuation-In-Part application of U.S. Ser. No. 08/615,904 filed Mar. 14, 1996, now abandoned.

FIELD OF THE INVENTION

The present invention relates to silicones functionalized with hydroxy carbamate substituents and cosmetic formulations made with such silicones.

BACKGROUND OF THE INVENTION

Silicones are often reacted with various functional groups to modify the characteristics of the resulting silicone while maintaining other desirable properties, e.g. viscosity, solubility, and refractive index. Various substituents provide useful changes in dipole moment and coordinating power, e.g. amino-functionalized and carboxylic acid functionalized silicones.

Cationic or free radical polymerization of

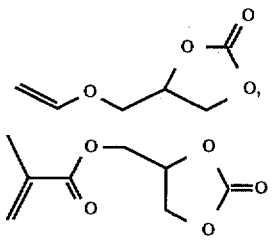

cyclic-(methacrylate)propylene carbonate ester, with various co-monomers has been employed to produce carbonate functionalized copolymers. These carbonate functionalized copolymers may be further reacted with amines to produce carbamate functionalized copolymers.

Reaction of polyhydrogen siloxanes (alternatively hydrogen siloxanes, hydride fluids or hydrides) with:

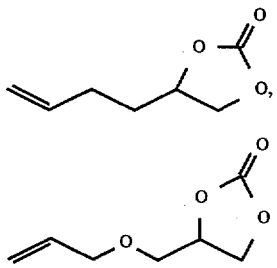

cyclic-((allyloxy)methyl)ethylene ester carbonate, produces carbonate functionalized silicones with dielectric constants varying from about 20 to about 50. These polymeric carbonate functionalized silicones displayed the ability to dissolve large quantities of lithium salts thus behaving as a polymeric electrolyte.

Silicones have properties that make them particularly advantageous in hair cosmetic products. Certain silicones produce uniform thin films that are hydrophobic and also produce solutions or emulsions that possess a low viscosity. The low viscosity property allows higher loadings of active ingredients in a cosmetic product without the deleterious effects normally associated with high viscosity products, difficulty of pumping or erratic spray patterns. This is important to the consumer because preparations that are hard to use or erratic in delivery from the dispensing apparatus will not be preferred.

The cosmetic and toiletry industry has produced a wide range of grooming aids that utilize silicones. Among the various products are shampoos to clean the hair and scalp, hair rinses, conditioners, dressings, sprays, wave sets, coloring and bleaching preparations, permanent waves, and hair straightening and strengthening compositions. Cleanliness of hair and scalp are important personal grooming criteria. Soiled hair takes on a lackluster appearance and becomes oily and unpleasant to the touch. Consumers desire a shampoo that foams quickly and copiously and rinses thoroughly leaving the hair with a fresh clean smell and in a manageable state. Further, consumers tend to prefer those shampoos that also leave the hair soft, shiny, lustrous, and full bodied. Shampoos are available in a variety of formulations as clear or opaque liquids, gels, or pastes. In order to fulfill the various criteria demanded by the consuming public, shampoo formulations contain one or more cleansing agents such as nonionic, anionic, and amphoteric surfactants along with various optional additives that include among others deposition agents such as cationic surfactants, viscosity control agents, conditioners, preservatives, fragrances, vitamins, antioxidants opacifiers, pearling agents, sunscreens, and botanicals as well as functionalizing additives such as conditioners, shine enhancers, and volumizing agents. After shampooing, the hair is usually wet, frequently tangled and thus difficult to comb. Thus it is common for consumers to apply rinses and conditioners to enhance the ease of combing and detangling, to increase hair body, to improve shine and texture, to prevent static buildup, to impart manageability, style retention, and curl retention.

Hair body is a subjective and poorly defined quality. It is generally accepted that volume is related to or provides a means for quantitatively measuring hair body. One method to increase the volume of hair tresses (and consequently the subjective property of hair body) is to impart a small degree of triboelectric charging to the hair. This can be accomplished through the use of a so-called volumizing shampoo which generally functions to strip the hair of natural oils leaving the hair fibers negatively charged with a consequent tendency for the hair fibers to electrostatically repel one another. This method does not produce consistent or predictable results since small changes in humidity will either aggravate the triboelectric charging resulting in fly-away hair (low RH) or dissipate the electrostatic charge resulting in flat hair (high RH). This technique also has a tendency to raise the cuticle scales damaging the hair and rendering it difficult to comb making it unmanageable. A more preferable technique to impart hair body is to deposit a hydrocarbon-based film on the hair via a preparation that remains on the hair between shampoos. These preparations, typically incorporating a hydrocarbon resin, generally impart drag and increase the forces necessary to comb the hair and thus make the hair difficult to groom while maintaining style. Additionally such products, depending on the choice of resins and base solvents can also result in the appearance of unsightly flakes on the hair. An additional problem is that such hydrocarbon solvent resin mixtures can dry the hair or impart brittleness, resulting in hair fiber breakage during subsequent grooming.

When using hydrocarbon based conditioning agents, increasing the organoalkyl content of quaternary ammonium conditioning compounds imparts an increasing conditioning ability to the compound. Conditioning efficacy of a quaternary ammonium compound increases with increasing alkyl chain length or with increasing alkyl substitution according to the series mono-alkyl <di-alkyl<tri-alkyl. Generally products that condition hair do not impart an improved body or hair volume unless they also contain resins.

One use of polymeric dialkylsiloxanes is to impart a conditioning property to hair care products. While the conventional polymeric dialkylsiloxanes impart good conditioning properties, such materials have a tendency to interact antagonistically with other additives such as fixatives diminishing their effectiveness. This conflict in properties between ingredients results in reformulations and stimulates efforts to prepare new materials that will be more compatible.

Conditioning shampoos are generally formulated to provide a cleansing of the hair followed by deposition of a material that acts to provide a conditioning benefit. Incorporation of a volumizing organofunctional MQ silicone resin that is compatible with the other components of a 2-in-1 shampoo, provides cleansing, conditioning and volumizing benefits.

Fixatives are generally designed to provide a temporary setting effect or maintain curl to the hair, the most common being a hair spray intended for use after the hair has been dried. Other fixatives may be used after the hair is towel dried to provide more body and volume and to aid in styling. Specialty type fixatives such as the foregoing include styling gels, mousses, cremes, foams, spritzes, mists, glazes, glossing gels, shaping gels, sculpting mousses, and setting gels among others. These fixatives should be compatible with a subsequent use of a fixative or luster enhancing hair spray.

Cuticle coats are formulations designed to impart or enhance shine on hair. Additionally, cuticle coats frequently reduce both tribo-electric charging effects, i.e. fly-away hair, and combing forces, by adding a lubricious coating to the hair, thus lowering both interfiber friction and electrostatic repulsion between the fibers. One method of imparting or increasing apparent luster or gloss on the hair is to coat the hair with a material having a high refractive index. Using this technique, the apparent gloss or shine will be proportional to the refractive index of the material on the fiber surface. Absent other factors, a direct proportionality exists between refractive index and apparent shine on hair. Thus higher refractive index cuticle coating formulations will tend to impart a higher shine on hair.

SUMMARY OF THE INVENTION

It has been discovered that hydroxy carbamate functionalized silicone compounds may be prepared by a hydrosilylation reaction between an unsaturated cyclic carbonate ester and a hydrogen containing siloxane to yield a carbonate functionalized silicone that may be further reacted with an amine to yield a silicone functionalized with hydroxy carbamate substituents. Such new silicone compounds are useful for a variety of applications particularly in personal care and cosmetic applications.

Thus the present invention provides for a hydroxy carbamate functionalized silicone of the general formula:

$M_a M'_b D_c D'_d T_e T'_f Q_g$ where $M=R_3SiO_{1/2}$, $M'=R_{3-i}R'_iSiO_{1/2}$, $D=R_2SiO_{2/2}$, $D'=R_{2-j}R'_jSiO_{2/2}$, $T=RSiO_{3/2}$, $T'=R'SiO_{3/2}$, and $Q=SiO_{4/2}$ where the subscript i varies from 1 to 3, the subscript j is either 1 or 2 and the subscripts a, b, c, d, e, f, and g are zero or positive subject to the limitation that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:

—$CH_2$—$CH_2$—R"—CH(OH)—$CH_2O_2CNR^1R^2$,

—$CH_2$—$CH_2$—R"—CH($O_2CNR^1R^2$)—$CH_2$—$O_H$ or mixtures thereof where R" is a divalent radical having from one to about forty carbon atoms and $R^1$ and $R^2$ are each independently selected from the group consisting of hydrogen and one to forty carbon atom monovalent hydrocarbon radicals.

The present invention provides for a process whereby the hydroxy carbamate functionalized silicone is produced via a hydrosilylation reaction of an unsaturated carbonate ester having the formula:

$$CH2=CH-R"-\underset{O}{\overset{O}{\bigcirc}}\!\!\!\!\!\!\!\!\!\!\!\!\!\!\!\!\!\!\!\!\!\!\!\!\!\!\!\!\!C\!\!=\!\!O$$

where R" is as previously defined with a hydrogen siloxane followed by reaction with HN $R^1R^2$ where $R^1$ and $R^2$ are as previously defined.

The hydroxy carbamate functionalized silicones of the present invention are useful components of various personal care compositions such as 2-in-1 shampoos, cuticle coats, styling gels, hair mousses, fixatives and the like.

The present invention provides for a silicone composition comprising a hydroxy carbamate functionalized silicone having the formula:

$M_a M'_b D_c D'_d T_e T'_f Q_g$ where $M=R_3SiO_{1/2}$, $M'=R_{3-i}R'_iSiO_{1/2}$, $D=R_2SiO_{2/2}$, $D'=R_{2-j}R'_jSiO_{2/2}$, $T=RSiO_{3/2}$, $T'=R'SiO_{3/2}$, and $Q=SiO_{4/2}$ where the subscript i varies from 1 to 3, the subscript j is either 1 or 2 and the subscripts a, b, c, d, e, f, and g are zero or positive subject to the limitations that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:

—$CH_2$—$CH_2$—R"—CH(OH)—$CH_2O_2CNR^1R^2$,

—$CH_2$—$CH_2$—R"—CH($O_2CNR^1R^2$)—$CH_2$—OH or mixtures thereof where R" is a divalent radical having from one to about forty carbon atoms and $R^1$ and $R^2$ are each independently selected from the group consisting of hydrogen and one to forty carbon atom monovalent hydrocarbon radicals.

The present invention further provides for a silicone composition comprising a carbonate functionalized silicone having the formula:

$M_a M''_b D_c D''_d T_e T''_f Q_g$ where $M=R_3SiO_{1/2}$, $M''=R_{3-i}R'''_iSiO_{1/2}$, $D=R_2SiO_{2/2}$, $D'' = R_{2-j}R'''_jSiO_{2/2}$,
$T = RSiO_{3/2}$,
$T'' = R'''SiO_{3/2}$, and
$Q = SiO_{4/2}$ where the subscript i varies from 1 to 3, the subscript j is 1 or 2 and the subscripts a, b, c, d, e, f, and g are zero or positive subject to the limitations that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R''' defined as:

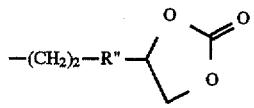

where R'' is a divalent radical having from one to about forty carbon atoms.

The present invention also provides a process for making a silicone comprising a hydroxy carbamate functionalized silicone comprising:

(a) reacting a hydrogen siloxane having the formula:
$M_zM^H_yD_xD^H_wT_vT^H_uQ_t$ where
$M = R_3SiO_{1/2}$,
$M^H = R_{3-k}H_kSiO_{1/2}$,
$D = R_2SiO_{2/2}$,
$D^H = R_{2-m}H_mSiO_{2/2}$,
$T = RSiO_{3/2}$,
$T^H = HSiO_{3/2}$, and
$Q = SiO_{4/2}$ where the subscript k varies from 1 to 3, the subscript m is either 1 or 2 and the subscripts t, u, v, w, x, y, and z are zero or positive subject to the limitations that the sum of u+w+y is positive (i.e. greater than zero), that one of y, x or v is one or greater and that the sum of t+v+x+z is zero or positive, with R being an independently selected monovalent hydrocarbon radical for each M, D, and T and ranging from 1 to about 40 carbon atoms, with an unsaturated cyclic carbonate ester having the formula:

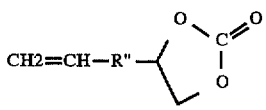

where R'' is a divalent radical having from one to about forty carbon atoms in the presence of a hydrosilylation catalyst;

(b) producing thereby a carbonate functionalized silicone having the formula:
$M_aM''_bD_cD''_dT_eT''_fQ_g$ where
$M = R_3SiO_{1/2}$,
$M'' = R_{3-i}R'''_iSiO_{1/2}$,
$D = R_2SiO_{2/2}$,
$D'' = R_{2-j}R'''_jSiO_{2/2}$,
$T = RSiO_{3/2}$,
$T'' = R'''SiO_{3/2}$, and
$Q = SiO_{4/2}$ where the subscript i varies from 1 to 3, the subscript j is 1 or 2 and the subscripts a, b, c, d, e, f, and g are zero or positive subject to the limitations that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R''' defined as:

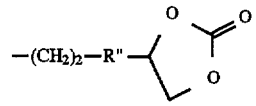

where R'' is a divalent radical having from one to about forty carbon atoms;

(c) reacting said carbonate ester functionalized silicone in the presence of an amine having the formula:
$HNR^1R^2$ where $R^1$ and $R^2$ are each independently selected from the group consisting of hydrogen and one to forty carbon atom monovalent hydrocarbon radicals; and (d) producing thereby a hydroxy carbamate functionalized silicone having the formula:
$M_aM'_bD_cD'_dT_eT'_fQ_g$ where
$M = R_3SiO_{1/2}$,
$M' = R_{3-i}R'_iSiO_{1/2}$,
$D = R_2SiO_{2/2}$,
$D' = R_{2-j}R'_jSiO_{2/2}$,
$T = RSiO_{3/2}$,
$T' = R'SiO_{3/2}$, and
$Q = SiO_{4/2}$ where the subscript i varies from 1 to 3, the subscript j is either 1 or 2 and the subscripts a, b, c, d, e, f, and g are zero or positive subject to the limitation that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:
—$CH_2$—$CH_2$—R''—CH(OH)—$CH_2O_2CNR^1R^2$,
—$CH_2$—$CH_2$—R''—CH($O_2CNR^1R^2$)—$CH_2$—OH or mixtures thereof where R'' is a divalent radical having from one to about forty carbon atoms and $R^1$ and $R^2$ are each independently selected from the group consisting of hydrogen and one to forty carbon atom monovalent hydrocarbon radicals; which process may be terminated at step (b) to provide a process for making a carbonate functionalized silicone.

DETAILED DESCRIPTION OF THE INVENTION

The compounds of the present invention are prepared by a hydrosilylation reaction between a hydrogen siloxane (a hydride fluid) and an unsaturated cyclic carbonate ester. Suitable hydride fluids are defined by the general formula:
$M_zM^H_yD_xD^H_wT_vT^H_uQ_t$ where
$M = R_3SiO_{1/2}$,
$M^H = R_{3-k}H_kSiO_{1/2}$,
$D = R_2SiO_{2/2}$,
$D^H = R_{2-m}H_mSiO_{2/2}$,
$T = RSiO_{3/2}$,
$T^H = HSiO_{3/2}$, and
$Q = SiO_{4/2}$ where the subscript k varies from 1 to 3, the subscript m is either 1 or 2 and the subscripts t, u, v, w, x, y, and z are zero or positive subject to the limitations that the sum of u+w+y is positive (i.e. greater than zero), that one of y, x or v is one or greater and that the sum of t+v+x+z is zero or positive, with R being an independently selected monovalent hydrocarbon radical for each M, D, and T and ranging from 1 to about 40 carbon atoms. The hydride, as defined above is reacted with an unsaturated cyclic carbonate ester having the formula:

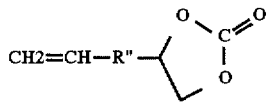

where R" is a divalent radical having from one to about forty carbon atoms. Particularly preferred examples of carbonate esters are selected from the group consisting of cyclic-((vinyloxy)methyl)ethylene ester carbonate, cyclic-((allyloxy)methyl)ethylene ester carbonate, cyclic-(3-butenyl)ethylene ester carbonate, and cyclic-(methacrylate) propylene carbonate ester.

The unsaturated carbonate ester is reacted with the hydride in the presence of a hydrosilylation catalyst producing thereby a carbonate ester functionalized silicone. Thus the foregoing produces a carbonate functionalized silicone of the formula:

$M_a M''_b D_c D'''_d T_e T'''_f Q_g$ where $M=R_3SiO_{1/2}$, $M''=R_{3-i}R'''_iSiO_{1/2}$, $D=R_2SiO_{2/2}$, $D''=R_{2-j}R'''_jSiO_{2/2}$, $T=RSiO_{3/2}$, $T''=R'''SiO_{3/2}$, and $Q=SiO_{4/2}$ where the subscript i varies from 1 to 3, the subscript j is 1 or 2 and the subscripts a, b, c, d, e, f, and g are zero or positive subject to the limitations that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R'''defined as:

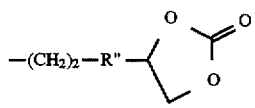

where R" is a divalent radical having from one to about forty carbon atoms.

The hydrosilylation catalyst is selected from the group consisting of catalyst comprising a metal selected from the group consisting of nickel, palladium, platinum, rhodium, iridium, ruthenium and osmium or as taught in U.S. Pat. Nos. 3,159,601; 3,159,662; 3,419,593; 3,715,334; 3,775,452 and 3,814,730 herewith and hereby incorporated by reference. A typical platinum-containing catalyst component useful for the preparation of the organopolysiloxane compositions of this invention is any form of chloroplatinic acid, such as, for example, the readily available hexahydrate form or the anhydrous form, because of its easy dispersibility in organosiloxane systems. A particularly useful form of chloroplatinic acid is that composition obtained when it is reacted with an aliphatically unsaturated organosilicon compound such as divinyltetramethyldisiloxane, as disclosed by U.S. Pat. No. 3,419,593. The catalyst employed may be any one of the Group VIII transition metals (Fe, Co, Ni, Ru, Rh, Pd, Os, Ir, and Pt) as the finely divided metal, as a supported metal catalyst supported on a wide variety of high surface area carriers such as silica, activated carbon, alumina, titania, or any other suitable high surface area porous solid (particularly porous inorganic oxides), or as a molecular or ionic species containing the Group VIII transition metal. The reaction product of the hydrosilylation reaction is a cyclic carbonate ester functionalized silicone.

After the cyclic carbonate ester functionalized silicone product is formed a subsequent reaction with an amine having the formula $HNR^1R^2$ where $R^1$ and $R^2$ are each independently selected from the group consisting of hydrogen and one to forty carbon atom monovalent hydrocarbon radicals, produces thereby the hydroxy carbamate functionalized silicone of the present invention.

Thus the foregoing produces a hydroxy carbamate functionalized silicone of the formula:

$M_a M'_b D_c D'_d T_e T'_f Q_g$ where $M=R_3SiO_{1/2}$, $M'=R_{3-i}R'_iSiO_{1/2}$, $D=R_2SiO_{2/2}$, $D'=R_{2-j}R'_jSiO_{2/2}$, $T=T=RSiO_{3/2}$, $T'=R'SiO_{3/2}$, and $Q=SiO_{4/2}$ where the subscript i varies from 1 to 3, the subscript j is 1 or 2 and the subscripts a, b, c, d, e, f, and g are zero or positive subject to the limitations that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:

—$CH_2$—$CH_2$—R"—$CH(OH)$—$CH_2O_2CNR^1R^2$,

—$CH_2$—$CH_2$—R"—$CH(O_2CNR^1R^2)$—$CH_2$—OH or mixtures thereof where R" is a divalent radical having from one to about forty carbon atoms and $R^1$ and $R^2$ are each independently selected from the group consisting of hydrogen and one to forty carbon atom monovalent hydrocarbon radicals.

A comparison of the formula of the hydride fluid precursor to the compounds of the present invention:

$M_z M^H_y D_x D^H_w T_v T^H_u Q^t$ with the compounds of the present invention:

$M_a M'_b D_c D'_d T_e T'_f Q_g$ reveals a correspondence between the hydride bearing groups of $M^H_y$, $D^H_w$, and, $T^H_u$ and the hydroxy carbamate functionalized groups of $M'_b$, $D'_d$, and $T'_f$. This correspondence requires that the stoichiometric subscripts y, w, and u correspond respectively to b, d, and f, i.e. y=b, w=d, and u=f.

It is to be noted that the divalent hydrocarbon radical R" may contain hetero-atoms, thus a two carbon divalent radical also includes —$CH_2$—O—$CH_2$—, —$CH_2$—S—$CH_2$—, —$CH_2$—NH—$CH_2$—, —$CH_2$—PH—$CH_2$—; further the hydrogen atoms on this divalent two carbon atom radical may be substituted by halogen such as fluorine, chlorine, bromine or iodine. A six carbon divalent hydrocarbon radical may be either an alicyclic aliphatic divalent radical such as —$(CH_2)_6$—, a divalent cyclohexyl group such as cyclo $C_6H_{10}$ where the attachment is independently selected from any of the six carbon atoms or a divalent phenyl group such as:

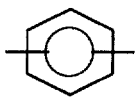

which indicates that the attachment may utilize any two carbon atoms. Thus any divalent radical possessing from one to forty carbon atoms is encompassed by the foregoing description.

While the general formula recited above admits M-functionalized, D-functionalized, T-functionalized hydroxy carbamate silicones and silicones with various mixtures of these various functionalizations, the preferred embodiment is a linear MDM type silicone represented by a more specific formula:

$M_a D_c D'_d$ where a=2, c ranges from about 10 to about 20, and d ranges from about 3 to about 10. Thus the formula of a preferred embodiment of the present invention is:

$MD_c D'_d M$ while another preferred embodiment has the formula:

$M'D_c M'$.

Applicants note that primed functional groups refer to hydroxy carbamate functionalized groups such as M', D', and T'. Functional groups bearing double primes are the cyclic carbonate functionalized groups, M", D", and T".

One particular use of the hydroxy carbamate functionalized silicones of the present invention is in personal care formulations. Modern cosmetic formulations for hair care typically utilize various silicones in two ways to increase shine or apparent luster. First, materials such as dimethicone fluids and gums are used to provide conditioning benefits resulting in increased fiber alignment and thus a smoother surface from which to reflect light. The second and more widely used method is to coat the hair with a material of high refractive index, typically a phenyl modified silicone such as phenyltrimethicone, phenylmethyl polysiloxane, or diphenyldimethicone. The concept underlying this approach is that the light is being reflected by the underlying melanin granules. Thus if the surface of the hair is coated with a material that has an index of refraction dose to that of the hair cuticle, there will be less scattering of light as the light passes through the various cuticle-cuticle or cuticle-cortex interfaces.

Shine enhancing additives may be effectively added to a variety of hair care products, most commonly cuticle coats and finishing sprays. Applicants note that products designed to improve the luster of human hair will also improve the luster or shine of non-human hair and so these formulations may also be used for animal grooming and appearance.

All United States patents referenced herein are herewith and hereby specifically incorporated by reference.

EXAMPLES

The following non-limiting examples demonstrate various embodiments of the present invention. The use of particular reactants is exemplary only and is not to be construed as a limitation of the broader and more general teachings of the previously set forth teachings.

The particular cyclic carbonate ester chosen for these demonstrations is cyclic((allyloxy)methyl)ethylene ester carbonate. This particular carbonate ester was reacted in the presence of various hydride fluids having either the formula:

$MD_c D^H_d M$ where the different hydride fluids were chosen on the basis of differing $D : D^H$ ratios since solubilities and refractive indeces are somewhat dependent on the ratio between D and $D^H$, or a hydride of the formula:

$M^H D_c M^H$.

Hydrosilylation of Unsaturated Carbonate Ester: Example Preparation 100 g (0.633 moles based on allyl functionality) of cyclic ((allyloxy)methyl)ethylene ester carbonate was charged into a 500 mL three neck round bottom flask equipped with a mechanical stirrer, thermometer and a dropping funnel along 66 mg of Karstedt's platinum catalyst containing sufficient platinum to yield a platinum concentration in the reaction mixture of 15 wppm. The reaction mixture was heated to 90° C. and 350 g of a hydride fluid ($MD_{20}D^H_3 M$) containing 0.575 equivalents of hydrogen as available hydride was added over a period of one hour. Reaction was approximately 90% complete after 2 hours as determined by Fourier Transform Infrared spectroscopy. The resulting product was filtered through Celite™ yielding a dear colorless fluid. In the unsaturated carbonate ester defined by the formula:

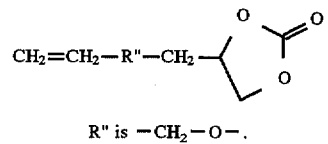

R" is $-CH_2-O-$.

This example is an example of functionalizing an $R_2 SiO_{2/2}$ group.

Preparation of terminally hydroxy carbamate functionalized silicones proceeded by charging a 500 mL flask with 200 g of a hydride stopped fluid, $M^H D_{25} M^H$ (0.20 equivalents of hydride), 10 mg of Karstedt's catalyst (0.0056 mmole) and 152 g of cyclohexane. The flask was equipped with a condenser, a thermometer, a stirring bar and a nitrogen blanketed addition funnel. The reaction mixture was heated to reflux, refluxing at 85° C. The addition funnel was charged with 34.9 g of cyclic-((allyloxy)methylethylene ester carbonate (0.22 mole) added over a 15 minute period. The reaction was allowed to proceed at the reflux temperature monitoring the hydride level. When the hydride level of the reaction mixture was below 50 ppm, the solvent was stripped from the reaction mixture under full vacuum at 100° C. until 97 weight percent solids was achieved. The viscosity of the product was 154 cSt and the refractive index was 1.4165. The above procedure was repeated for $M^H D_5 M^H$ resulting in a product with a viscosity of 150 cSt and a refractive index of 1.4810.

Amidation of Carbonate Ester, Carbamate Formation: Example Preparation:

50 mL of neat diethylamine was charged into a 100 mL single neck round bottom flask along with 20 g of a carbonate ester functionalized silicone fluid. The reaction was stirred at reflux for at least 16 hours and as long as 48 hours. Excess diethylamine was recovered on a rotary evaporator and the product filtered through Celite™ In the case of dioctyl amine, the reaction mixture was heated at 100° C. This example is an example of hydroxy carbamate functionalized silicone containing a hydroxy carbamate functionalized D group where the D group is D' and is $R_{2-j} R'_j SiO_{2/2}$, R being methyl and j=1 with $R^1$ and $R^2$ being ethyl.

A similar procedure was employed with the terminally functionalized hydroxy carbamate silicones using excess diethylamine.

TABLE 1

Silicones Functionalized with Cyclic Carbonate Groups

| Structure | D: D' | Wt. % Silicone | Viscosity, centistokes (cSt) | Refractive Index |
|---|---|---|---|---|
| $D''_4$ | 0.0 | 27.5 | 7466 | 1.4711 |
| $MD_{20}D''_{10}M$ | 2.0 | 59.1 | 1797 | 1.4379 |
| $MD_{11}D''_4M$ | 2.75 | 68.7 | 282 | 1.4301 |
| $MD_{20}D''_{4.5}M$ | 4.5 | 75.1 | 430 | 1.4256 |
| $MD_{20}D''_3M$ | 6.7 | 79.4 | 225 | 1.4210 |
| $M''D_{25}M''$ | not relevant | 86.0 | 154 | 1.4165 |
| $M''D_5M''$ | not relevant | 61.0 | 150 | 1.4344 |

The carbonate functionalized silicone fluids, shown in Table 1, were reacted with secondary amines by heating the secondary amine in the presence of the silicone at reflux temperatures or at temperature ranging from about 80° C. to about 120° C. for a period of at least 16 hours. The extent of the reaction was monitored using Fourier Transform Infrared FTIR) spectroscopy by following the disappearance of the carbonate resonance at approximately 1800 cm$^{-1}$ and the associated appearance of the carbamate absorbance at approximately 1700 cm$^{-1}$.

Two different secondary amines were used, diethyl amine (DEA) and dioctyl amine (DOA). Excess diethyl amine was easily removed from the reaction by the application of a vacuum. The higher vapor pressure of dioctyl amine necessitated the use of a slight molar deficiency in the quantity of dioctyl amine, 95% of theoretical. The results of these preparations are summarized in Table 2.

TABLE 2

Silicones Functionalized with Carbamate Groups

| Structure | D: D' | Wt. % Silicone | Viscosity, cSt | Refractive Index | Amine, DEA or DOA |
|---|---|---|---|---|---|
| $D'_4$ | 0 | 20.7 | 3405 | 1.4699 | DEA |
| $MD_{20}D'_{10}M$ | 2.0 | 49.8 | 2677 | 1.4433 | DEA |
| $MD_{20}D'_{10}M$ | 2.0 | 39.5 | 641 | 1.4446 | DOA |
| $MD_{11}D'_4M$ | 2.75 | 60.1 | na | 1.4393 | DEA |
| $MD_{20}D'_{4.5}M$ | 4.5 | 67.4 | 288 | 1.4304 | DEA |
| $MD_{20}D'_3M$ | 6.7 | 77.0 | 231 | 1.4268 | DEA |
| $MD_{20}D'_3M$ | 6.7 | 71.9 | 231 | 1.4356 | DOA |
| $M'D_{25}M'$ | not relevant | 81.0 | not available | 1.4810 | DEA |
| $M'D_5M'$ | not relevant | 56.0 | not available | not available | DEA |

The hydroxy carbamate functionalized silicones of the present invention were tested to ascertain solubility in various solvents as they might be used in personal care products. The silicones were tested as a mixture containing 20 weight percent of the silicone and 80 weight percent of the solvent. None of the carbonate ester functionalized silicones were soluble in decamethylcyclopentasiloxane, isodecane or mineral oil. Thus, based on solubility considerations alone the carbonate ester functionalized silicones may not be incorporated into personal care compositions simply by dissolving them in cosmetically acceptable solvents or carriers. In contrast while the carbamate functionalized silicones were also insoluble in isodecane or mineral oil, they were generally soluble in isopropyl alcohol (IPA) and two were miscible with decamethylcyclopentasiloxane ($D_5$).

TABLE 3

Solubilities of Carbonate Functionalized Silicone Fluids

| Structure | $D_5$ | IPA | Isodecane | Mineral Oil |
|---|---|---|---|---|
| $D''_4$ | no | no | no | no |
| $MD_{20}D''_{10}M$ | no | no | no | no |
| $MD_{11}D''_4M$ | no | no | no | no |
| $MD_{20}D''_{4.5}M$ | no | yes | no | no |
| $MD_{20}D''_3M$ | no | yes | no | no |

Note: no = insoluble, yes = soluble

TABLE 4

Solubilities of Carbamate Functionalized Silicone Fluids

| Structure | $D_5$ | IPA | Isodecane | Mineral Oil |
|---|---|---|---|---|
| $D'_4$ | no | no | no | no |
| $MD_{20}D'_{10}M$ | no | yes | no | no |
| $MD_{20}D'_{10}M$ | no | yes | no | no |
| $MD_{11}D'_4M$ | no | yes | no | no |
| $MD_{20}D'_{4.5}M$ | no | yes | no | no |
| $MD_{20}D'_3M$ | yes | yes | no | no |
| $MD_{20}D'_3M$ | yes | yes | no | no |

Note: no = insoluble, yes = soluble

TABLE 5

Solubilities of Terminally Functionalized Silicone Fluids

| Structure | Functionality | $D_5$ | Dimethicone 5 cSt | Dimethicone 20 cSt |
|---|---|---|---|---|
| $M''D_{25}M''$ | carbonate | yes | yes | no |
| $M'D_{25}M'$ | carbamate | yes | yes | yes |
| $M''D_5M''$ | carbonate | yes | no | no |
| $M'D_5M'$ | carbamate | yes | no | no |

Cosmetic Formulations:

The hydroxy carbamate functionalized silicones $MD_{20}D'_3M$ (carbamate of diethylamine) and $MD_{20}D'_3M$ (carbamate of dioctylamine) were diluted to 20 weight percent in cyclomethicone which is an 85:15 weight ratio mixture of octamethylcyclotetrasiloxane ($D_4$) and decamethylcyclopentasiloxane ($D_5$) and sprayed onto 6 inch long human hair tresses weighing an average of 2 g each. The products were applied via a spray pump, depressing the valve three times for each side of the hair tress, delivering a total of 0.6 g of solution per tress. An in-house panel of 21 participants rated the tresses treated with the compounds of the present invention as more lustrous, or having higher levels of shine as compared to the controls. The controls were: 1) a shampooed Caucasian tress receiving no conditioning treatment, i.e. virgin brown hair, 2) a shampooed tress treated with a commercially available shine spray (Citrishine™), and 3) a shampooed tress treated with a silicone based cuticle coat product comprising phenyltrimethicone, a known luster enhancing agent (formulation #1). Since the refractive indeces of the compounds of the present invention are below that of human hair which ranges from 1.51 to 1.52, an improvement in luster would not have been expected based on the requirement of a close match in refractive indeces.

TABLE 6

Hair Luster Evaluations

| Treatment | Rating |
| --- | --- |
| Untreated Control | 2.9 |
| Cuticle Coat | 3.5 |
| Commercial Shine Spray | 3.3 |
| $MD_{20}D'_3M$ (carbamate of diethylamine) | 4.4 |
| $MD_{20}D'_3M$ (carbamate of dioctylamine) | 4.4 |

TABLE 7

Cuticle Coat Formulation:

| Material CTFA Nomenclature | Amount weight percent |
| --- | --- |
| Cyclomethicone and Dimethicone 85:15 parts by weight respectively | 60.0 |
| Cyclomethicone 85:15 parts by weight of $D_4$:$D_5$ respectively | 19.0 |
| Iso-hexadecane | 10.0 |
| Phenyltrimethicone | 5.0 |
| Iso-propyl myristate | 5.0 |
| Trimethylsilylamodimethicone | 1.0 |

Having described the invention that which is claimed is:

1. A silicone composition comprising a hydroxy carbamate functionalized silicone having the formula:

$M_aM'_bD_cD'_dT_eT'_fQ_g$ where $M=R_3SiO_{1/2}$, $M'=R_{3-i}R'_iSiO_{1/2}$, $D=R_2SiO_{2/2}$, $D'=R_{2-j}R'_jSiO_{2/2}$, $T=RSiO_{3/2}$, $T'=R'SiO_{3/2}$, and $Q=SiO_{4/2}$ where the subscript i varies from 1 to 3, the subscript j is either 1 or 2 and the subscripts a, b, c, d, e, f, and g are zero or positive subject to the limitation that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:

—$CH_2$—$CH_2$—R"—$CH(OH)$—$CH_2O_2CNR^1R^2$,

—$CH_2$—$CH_2$—R"—$CH(O_2CNR^1R^2)$—$CH_2$—OH or mixtures thereof where R" is a divalent radical having from one to about forty carbon atoms and $R^1$ and $R^2$ are each independently selected from the group consisting of hydrogen and one to forty carbon atom monovalent hydrocarbon radicals.

2. The silicone of claim 1 where the subscripts b, e, f, and g are each zero.

3. The silicone of claim 2 where the subscript c ranges from 1 to about 30.

4. The silicone of claim 3 where the subscript d ranges from 1 to about 10.

5. The silicone of claim 4 where the subscript j is one.

6. The silicone of claim 1 where the subscripts a, d, e, f, and g are each zero.

7. The silicone of claim 6 where the subscript c ranges from 1 to about 30.

8. The silicone of claim 7 where the subscript c ranges from 1 to about 5.

9. The silicone of claim 8 where the subscript i is one.

10. A silicone composition consisting essentially of a hydroxy carbamate functionalized silicone having the formula:

$M_aM'_bD_cD'_dT_eT'_fQ_g$ where $M=R_3SiO_{1/2}$, $M'=R_{3-i}R'_iSiO_{1/2}$, $D=R_2SiO_{2/2}$, $D'=R_{2-j}R'_jSiO_{2/2}$, $T=RSiO_{3/2}$, $T'=R'SiO_{3/2}$, and $Q=SiO_{4/2}$ where the subscript i varies from 1 to 3, the subscript j is either 1 or 2 and the subscripts a, b, c, d, e, f, and g are zero or positive subject to the limitation that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:

—$CH_2$—$CH_2$—R"—$CH(OH)$—$CH_2O_2CNR^1R^2$,

—$CH_2$—$CH_2$—R"—$CH(O_2CNR^1R^2)$—$CH_2$—OH or mixtures thereof where R" is a divalent radical having from one to about forty carbon atoms and $R^1$ and $R^2$ are each independently selected from the group consisting of hydrogen and one to forty carbon atom monovalent hydrocarbon radicals.

11. A silicone composition comprising a carbonate functionalized silicone having the formula:

$M_aM''_bD_cD''_dT_eT''_fQ_g$ where $M=R_3SiO_{1/2}$, $M''=R_{3-i}R'''_iSiO_{1/2}$, $D=R_2SiO_{2/2}$, $D''=R_{2-j}R'''_jSiO_{2/2}$, $T=RSiO_{3/2}$, $T''=R'''SiO_{3/2}$, and $Q=SiO_{4/2}$ where the subscript i varies from 1 to 3, the subscript j is 1 or 2 and the subscripts a, b, c, d, e, f, and g are zero or positive subject to the limitations that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R''' defined as:

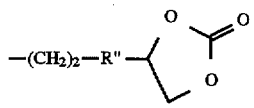

where is a divalent radical having from one to about forty carbon atoms.

12. The silicone of claim 11 where the subscripts b, e, f, and g are each zero.

13. The silicone of claim 12 where the subscript c ranges from 1 to about 30.

14. The silicone of claim 13 where the subscript d ranges from 1 to about 10.

15. The silicone of claim 14 where the subscript j is one.

16. The silicone of claim 11 where the subscripts a, d, e, f, and g are each zero.

17. The silicone of claim 16 where the subscript c ranges from 1 to about 30.

18. The silicone of claim 17 where the subscript c ranges from 1 to about 5.

19. The silicone of claim 18 where the subscript is one.

20. The silicone of claim 11 where R''' is selected from the group consisting of cyclic-((ethylene-oxy)methyl)ethylene ester carbonate, cyclic-((propyleneoxy)methyl)ethylene ester carbonate, cyclic-(3-butylene)ethylene ester carbonate, and cyclic-(methacrylate)propylene carbonate ester.

21. A process for making a silicone comprising a hydroxy carbamate functionalized silicone comprising:

(a) reacting a hydrogen siloxane having the formula:
$M_zM^H{}_yD_xD^H{}_wT_vT^H{}_uQ_t$ where
$M=R_3SiO_{1/2}$,
$M^H=R_{3-k}H_kSiO_{1/2}$,
$D=R_2SiO_{2/2}$,
$D^H=R_{2-m}H_mSiO_{2/2}$,
$T=RSiO_{3/2}$,
$T^H=HSiO_{3/2}$, and
$Q=SiO_{4/2}$ where the subscript k varies from 1 to 3, the subscript m is either 1 or 2 and the subscripts t, u, v, w, x, y, and z are zero or positive subject to the limitations that the sum of u+w+y is greater than zero, that one of y, x or v is one or greater and that the sum of t+v+x+z is zero or positive, with R being an independently selected monovalent hydrocarbon radical for each M, D, and T and ranging from 1 to about 40 carbon atoms, with an unsaturated cyclic carbonate ester having the formula:

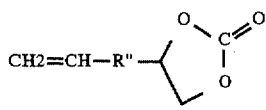

where R'' is a divalent radical having from one to about forty carbon atoms in the presence of a hydrosilylation catalyst;

(b) producing thereby a carbonate functionalized silicone having the formula:
$M_aM''{}_bD_cD''{}_dT_eT''{}_fQ_g$ where
$M=R_3SiO_{1/2}$,
$M''=R_{3-i}R'''{}_iSiO_{1/2}$,
$D=R_2SiO_{2/2}$,
$D''=R_{2-j}R'''{}_jSiO_{2/2}$,
$T=RSiO_{3/2}$,
$T''=R'''SiO_{3/2}$, and
$Q=SiO_{4/2}$ where the subscript i varies from 1 to 3, the subscript j is 1 or 2 and the subscripts a, b, c, d, e, f, and g are zero or positive subject to the limitation that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R''' defined as:

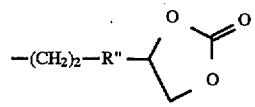

where is a divalent radical having from one to about forty carbon atoms;

(c) reacting said carbonate ester functionalized silicone in the presence of an amine having the formula:
$HNR^1R^2$
where $R^1$ and $R^2$ are each independently selected from the group consisting of hydrogen and one to forty carbon atom monovalent hydrocarbon radicals; and (d) producing thereby a hydroxy carbamate functionalized silicone having the formula:
$M_aM'{}_bD_cD'{}_dT_eT'{}_fQ_g$ where
$M=R_3SiO_{1/2}$,
$M'=R_{3-i}R'{}_iSiO_{1/2}$,
$D=R_2SiO_{2/2}$,
$D'=R_{2-j}R'{}_jSiO_{2/2}$,
$T=RSiO_{3/2}$,
$T'=R'SiO_{3/2}$, and
$Q=SiO_{4/2}$ where the subscript i varies from 1 to 3, the subscript j is either 1 or 2 and the subscripts a, b, c, d, e, f, and g are zero or positive subject to the limitation that the sum of b+d+f is at least one, and b, c, or e is one or greater, and the sum of a+c+e+g is zero or positive, with R being an independently selected monovalent hydrocarbon radical for each M, D, and T and ranging from 1 to about 40 carbon atoms with R' defined as:

—$CH_2$—$CH_2$—R''—CH(OH)—$CH_2O_2CNR^1R^2$,

—$CH_2$—$CH_2$—R''—CH($O_2CNR^1R^2$)—$CH_2$—OH or mixtures thereof where R'' is a divalent radical having from one to about forty carbon atoms and $R^1$ and $R^2$ are each independently selected from the group consisting of hydrogen and one to forty carbon atom monovalent hydrocarbon radicals.

* * * * *